United States Patent [19]

Fujimori et al.

[11] Patent Number: 5,316,983
[45] Date of Patent: May 31, 1994

[54] APPARATUS FOR ANALYSIS OF PARTICULATE MATERIAL, ANALYTICAL METHOD FOR SAME, APPARATUS FOR PRODUCTION OF ULTRAPURE WATER, APPARATUS FOR MANUFACTURING OF SEMICONDUCTOR, AND APPARATUS FOR PRODUCTION OF PURE GAS

[75] Inventors: Haruo Fujimori; Tetsuya Matsui; Taiko Ajiro; Kenji Yokose, all of Hitachi; Shigeru Izumi, Tokyo, all of Japan

[73] Assignee: Hitachi, Ltd., Tokyo, Japan

[21] Appl. No.: 740,493

[22] Filed: Aug. 5, 1991

[30] Foreign Application Priority Data

Aug. 3, 1990 [JP] Japan .................................. 2-205036

[51] Int. Cl.$^5$ .......................................... H01L 21/00
[52] U.S. Cl. .................................. 437/250; 356/335; 356/336
[58] Field of Search ............... 356/318, 336, 73, 335; 250/241, 341, 458.1; 437/250

[56] References Cited

U.S. PATENT DOCUMENTS

| | | |
|---|---|---|
| 4,652,755 | 3/1987 | Solomon et al. ................ 250/341 |
| 4,808,828 | 2/1989 | Kitamori et al. ............. 250/458.1 |
| 4,855,023 | 8/1989 | Clark et al. ..................... 204/130 |
| 5,015,094 | 5/1991 | Oka et al. ........................ 356/336 |
| 5,070,300 | 12/1991 | Matsui et al. .................... 324/464 |
| 5,148,031 | 9/1992 | Kamalov et al. ............. 250/458.1 |

Primary Examiner—Olik Chaudhuri
Assistant Examiner—H. Jey Tsai
Attorney, Agent, or Firm—Antonelli, Terry, Stout & Kraus

[57] ABSTRACT

An apparatus and a method for analysis of a particle by irradiation of the particle in a fluid with an intense laser pulse to cause laser breakdown and to detect sonic waves or plasma emission which are generated by the laser breakdown. The size of the particle is measured by using at least two kinds of information from the following: intensity of plasma emission or sonic wave generated by the laser breakdown, location of the laser breakdown plasma, and plasma emission waveform. Also, a laser pulse having flattened distribution of intensity for the irradiation is used in order to eliminate the dependence of the measured value on the particle location.

29 Claims, 12 Drawing Sheets

LASER BREAKDOWN OF SAME PARTICLE SIZE

INITIATING TIME OF EMISSION

LASER BREAKDOWN AT SAME POSITION

A > B

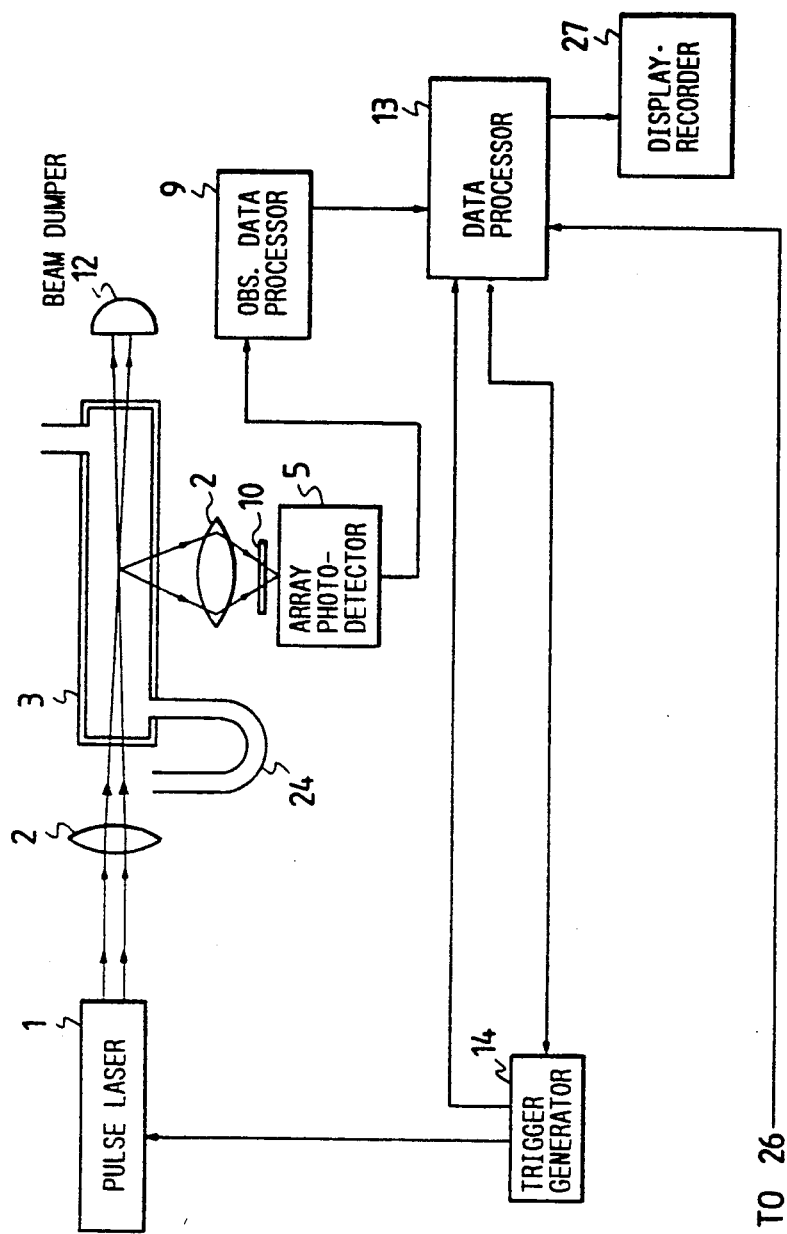

APPARATUS FOR ANALYSIS OF PARTICULATE MATERIAL, ANALYTICAL METHOD FOR SAME, APPARATUS FOR PRODUCTION OF ULTRAPURE WATER, APPARATUS FOR MANUFACTURING OF SEMICONDUCTOR, AND APPARATUS FOR PRODUCTION OF PURE GAS

BACKGROUND OF THE INVENTION (1) Field of the Invention

The present invention relates to an apparatus and a method for analysis of particulate material in fluid, especially, to the apparatus and the method for analysis of the particulate material, which are preferable for measurement of particle size of the particulate material existing in pure liquid such as ultra pure water used in a manufacturing process of semiconductor or in production of pure gas.

(2) Description of the Prior Art

As a method for measurement of particle size of ultra fine particles, which is the particulate material, a laser breakdown method which utilizes plasma formation by irradiates a particle with an intense laser pulse is effective. As for such methods, prior art are disclosed in JP-A-62-38345 (1987) and JP-A-1-116433 (1989). In JP-A-62-38345 (1987), the number of particles is counted by detecting sonic waves which are generated by a laser breakdown which is caused only when the particle is existing in a sensitive region where energy is larger than the laser breakdown threshold value) by collecting pulsed laser beam, and setting energy density of the laser beam higher than the laser breakdown threshold value of the particle and lower than the laser breakdown threshold value of the medium Further, the particle size is measured by using a tendency that generated intensity of the sonic wave is proportional to the particle size On the other hand, in JP-A-1-116433 (1989), the particle size is measured by detecting only intensity of emission line spectrum of elements which is included in generated plasma emission at the breakdown.

The prior art described above has a problem that precision of the particle size measurement is not necessarily high because of neglecting the fluctuation in intensity of the sonic wave and intensity of the plasma emission which are caused by difference of absorbed quantity of light by plasma depending on the position (the position of the particle in the sensitive portion) where the breakdown occurred Especially, the prior art has a problem that ultra fine particle having a particle diameter less than 0.1 μm is not detectable with preferable reproducibility.

Further, as the prior art disclosed in JP-A-1-116433 (1989) uses bright line spectrum which is only a part of plasma emission, sensitivity is not necessarily high, and detection of ultrafine particle having a particle diameter of 0.1 μm at largest was impossible.

SUMMARY OF THE INVENTION

The object of the present invention is to provide an analytical apparatus having an ability of precise measurement of particle size of particulate material, and a method thereof.

The other object of the present invention is to provide an analytical apparatus for the particulate material, which is able to measure particle size of 0.1 μm at smallest with preferable reproducibility.

The other object of the present invention is to provide an apparatus for producing ultrapure water which is able to guarantee the particle size in the ultrapure water, and an highly reliable apparatus for manufacturing of semiconductor using the ultrapure water.

The object of the present invention is achieved by measurement of the particle size of the particulate material in fluid by using at least two kinds of information on emission intensity of laser breakdown plasma, on location of the laser breakdown plasma, and on emission waveform of the laser breakdown plasma.

And, the object of the present invention is achieved by providing a means of flattening of power density of a laser pulse.

Further, the object of the present invention is achieved by measuring the spatial distribution of the plasma.

Relation between the particle size and threshold of the laser breakdown, which is power density of the laser pulse required to cause the laser breakdown, is in a negative relation as shown in FIG. 2.

FIG. 3 shows a region near the focusing spot of the laser pulse. The spatial and temporal profiles of the power density of a laser pulse are shown in FIG. 4(a), (b), and (c) where (r, z) are the cylindrical coordinates defined in FIG. 3, t is the elapsing time. Based on the spatial distribution, a sensitive region, which is a region wherein a particle having a specific size induces laser breakdown, occupies the region shown in FIG. 3. Near the boundary of the sensitive region, the power density of the laser pulse reaches the laser breakdown threshold later than the focusing center, due to the spatial distribution of the power density. Then, the time when the laser breakdown occurs differs by the location of the particle even if the particle diameter is constant.

The emission intensity of the laser breakdown plasma, which reflects the laser energy absorbed by the plasma, also depends on the particle location. The present invention is achieved on the base of the novel finding described above.

The novel finding is explained using mathematical equations hereinafter.

The emission intensity of the laser breakdown plasma, $I_p$, $r_0$, $z_0$) is given by the following equation.

$$I_p(d, r_0, z_0) = k_1 \int_{t_0(d, r_0, z_0)}^{\infty} dt' \int_0^{r_p(t')} dr' \int_0^{2\pi} d\theta' P(r, z_0, t') r', \quad (1)$$

$$r^2 = r_0^2 + r'^2 - 2r_0 r' \cos\theta'$$

Where, $k_1$ is a constant, $r_0$ and $z_0$ are coordinates of the particle location, $r_p$ is diameter of the plasma, $P(r, z_0, t)$ is the power density of the laser pulse at the position $(r, z_0)$ at the time $t$, $r'$ and $\Theta'$ are polar coordinates having an origin at $(r_0, z_0)$. $t_0$ is the time when the power density of the laser pulse at the position $(r_0, z_0)$ exceeds the laser breakdown threshold value of the particle having a diameter of d, that is, the initiation time of the plasma emission. The diameter of the plasma, $r_p$, in the equation (1), which increases during the laser pulse, is expressed by the equation (2), $$r_p(t) = k_2 \int_{t_0(d, r_0, z_0)}^{t} dt' \int_0^{r_p(t')} dr' \int_0^{2\pi} d\theta' P(r, z_0, t') r', \quad (2)$$

where, $k_2$ is a constant.

The equation (1) means that the intensity of the plasma emission, $I_p$, is proportional to the laser pulse energy absorbed by the laser breakdown plasma. The emission intensity of the laser breakdown plasma $I_p$ depends on the particle size d, because the initiation time, $t_0$, depends on it. It also depends on the particle position ($r_0$, $z_0$). Then, to obtain the particle size d, it is necessary to find the plasma emission intensity, the particle location ($r_0$, $z_0$), or the initiation time of the laser breakdown $t_0$. The plasma emission waveform is influenced with the initiation time of the laser breakdown $t_0$ as understood from the equations (1) and (2). Therefore, indexes expressing such feature of the plasma emission waveform as rise time (for instance, time for relative intensity change from 10% to 90% of peak intensity), and fall time (for instance, time for relative intensity change from 90% to 10% of peak intensity) can be an alternative information of $t_0$. Hereinafter, indexes which express the feature of plasma emission waveform are called the waveform information of the plasma emission.

As the waveform of the laser pulse is almost the same for each pulse in general, particle size dependence of the plasma emission intensity ($I_p$), the coordinate of the plasma location ($r_0$, $z_0$) or the waveform information such as $t_0$ is previously determined, and subsequently the particle size is obtained from more than one kind of the information described above.

And, by obtaining more than two kinds of information precision of the particle size measurement can be improved. The present invention which uses at least two kinds of information on the plasma emission intensity, the plasma location or the plasma emission waveform is clearly preferable to the prior art which uses only the plasma emission intensity in aspect of improvement of precise measurement.

Next, sonic wave generated by the laser breakdown is explained.

The sonic wave intensity, $I_a$, depends on time derivative of the volume of medium which is excluded by the plasma, and is given by the equation (4).

$$I_a(d,r_0,z_0) = k_3 \int_T \frac{dr_p}{dt} dt$$

$$= k_2 k_3 \int_{t_0(d,r_0,z_0)}^t dt' \int_0^{r_p(t')} dr' \int_0^{2\pi} d\theta' P(r,z_0,t')r'$$

$$\approx \frac{k_2 k_3}{k_1} I_p(d_0,r_0,z_0)$$

(3)

The sonic wave intensity, $I_a$, is proportional to the plasma emission intensity, $I_p$. Then, the plasma emission intensity can be replaced by the sonic wave intensity, so that the precision of the particle size measurement can be improved by obtaining at least two kinds of information among the sonic wave intensity, the location of the plasma, and the plasma emission sonic waveform.

In the case described above, the information on the location of the breakdown generation is necessary because of the spatial profile of the laser pulse power density. Accordingly, the precision of the particle size measurement can be improved by providing a means of flattening of the spatial profile of the laser pulse power density in the sensitive region.

In the present invention, following effects in measurement of particle size are brought by using information relating to the particle size in addition to the plasma emission intensity.

First, an apparatus for analysis of particulate material which is able to measure the particle size with preferable reproducibility can be provided.

And, an apparatus for analysis of particulate material which is able to measure the particle size especially of 0.1 $\mu$m at smallest with preferable reproducibility can be provided.

Further, an apparatus for producing ultrapure water which is able to guarantee the particle size of particulate material in the ultrapure water can be provided.

Finally, an apparatus for manufacturing of semiconductor having high reliability can be provided.

BRIEF DESCRIPTION OF THE DRAWINGS

FIG. 12 is a schematic representation of the composition of the apparatus for measurement and counting of the particle in the sixth embodiment of the present invention.

FIG. 13 (b) is a graph showing the relation between the axial position of plasma emission and the initiation time of the plasma emission at the radial direction of the plasma emission $r_0 = 0$, and.

DESCRIPTION OF THE PREFERRED EMBODIMENT

Embodiment 1

Hereinafter, the first embodiment of the present invention is explained with FIG. 1.

Figure 1:
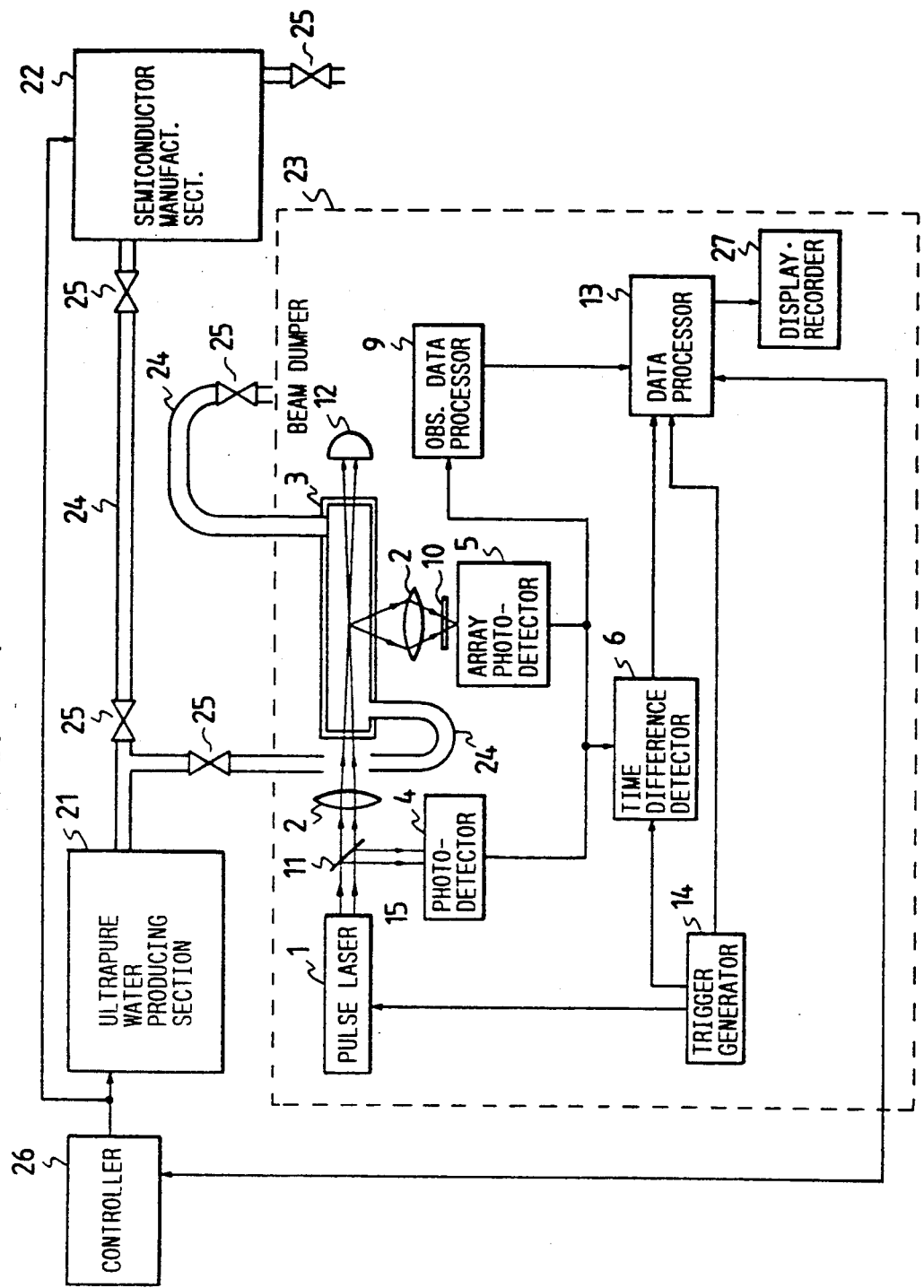
FIG. 1 is a schematic representation of the composition of the apparatus in one of the embodiments of the present invention.

In FIG. 1, a semiconductor manufacturing apparatus having ultrapure water producing section is shown. The apparatus comprises the ultrapure water producing section 21, a semiconductor manufacturing section 22, a section for measurement and counting of particle 23, pipings for connecting the sections 24, valves 25, and a controller 26. Further, the section for measurement and counting of particles 23 comprises a pulse laser 1, focusing lenses 2, a sample cell 3, an array photodetector 5, a time difference detector 6, an observed data processor 9, a cutting filter of laser beam 10, a beam splitter 11, a beam dumper 12, a data processor 13, a trigger generator 14, and a display-recorder 27. The sample cell including the attached optical system is installed in a dark box (not shown in FIG. 1).

Ultrapure water produced at the ultrapure water producing section 21 is sent to the semiconductor manufacturing section 22, and utilized in a process of wafer cleaning etc. Simultaneously, a part of the ultrapure water is taken as a sample, sent to the section for measurement and counting of particle 23, and examined in particle size and concentration of particulate impurities in the ultrapure water. The observed result is sent to the controller, and when the concentration of the particulate impurities is higher than the predetermined level, such measures as changing of filters in the ultrapure water producing section 21 are taken, announcing with warning signals, and stopping the operation of the ultrapure water producing section 21 and semiconductor manufacturing section 22. In the determination of the predetermined level for changing the filter, when the particle diameter 0.1 μm at largest is required for instance, select about 0.8 μm with a margin. By selecting the predetermined level like as described above, the apparatus for manufacturing of semiconductor can be operated continuously. And, as the observed data is recorded by the display-recorder 27 in the section of the measurement and counting of the particle 23, analysis of the relation of the yield of the semiconductor with the particle size and the concentration of the particulate impurities is possible.

The section of measurement and counting of the particle 23 of the present embodiment performs the measurement of the particle size with the intensity of the plasma emission, the position of the plasma, and the initiation time of the plasma emission.

Figure 2:
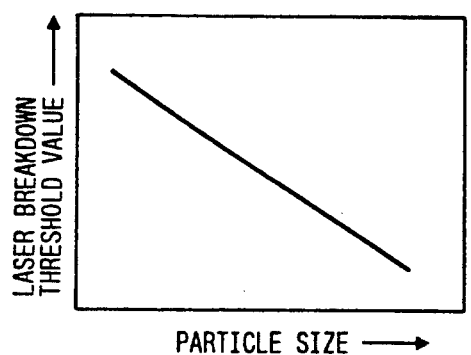
FIG. 2 is a graph showing the dependence of the threshold value of the laser breakdown on the particle size.
Figure 3:
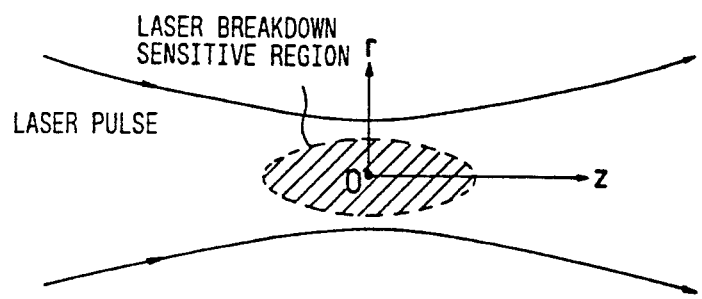
FIG. 3 is a drawing showing the sensitive region of the breakdown.
Figure 4A:
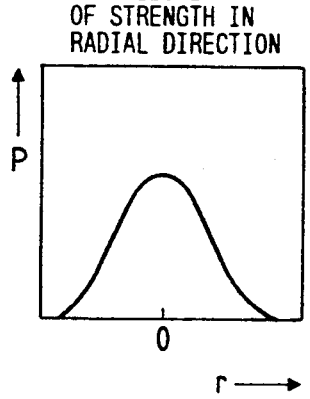
FIGS. 4(a), (b) and (c) are drawings for explanation of the chronical and spatial distribution of the laser pulse power density.
Figure 4B:
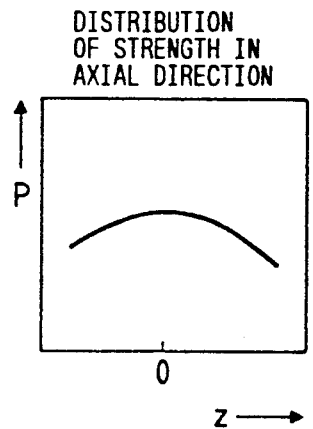
Figure 4C:
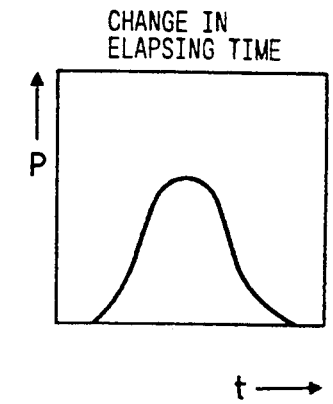
Figure 5A:
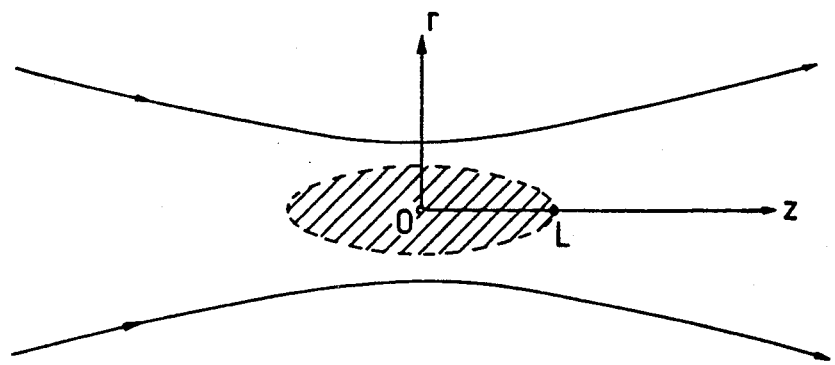
FIG. 5(a), (b) and (c) are drawings for explanation of the dependence of the waveform of plasma emission on the particle size and the location.
Figure 5B:
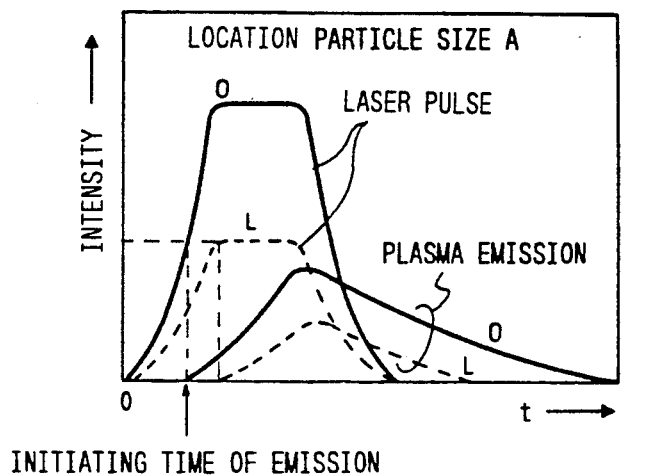
Figure 5C:
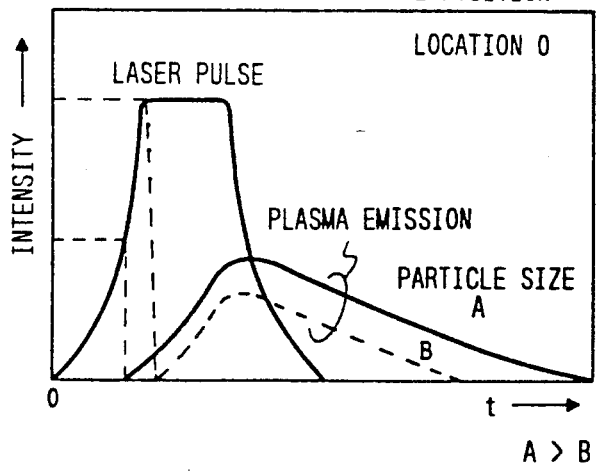

The laser pulse 15 from the pulse laser 1 is separated partly at the beam splitter 11, focused in the sample cell 3 by the focusing lens 2, and absorbed by the beam dumper 12. The sample cell and annex including the photodetector is installed in the black box (omitted in the figure). When a particle in the ultrapure water enters the focused region and the intensity of the beam exceeds the threshold value of laser breakdown, a laser breakdown occurs. The threshold value of the laser breakdown has a dependence on the particle size as shown in FIG. 2, and the intensity of the laser pulse intensity (power density) in the laser breakdown sensitive region which is formed in the focused region of the laser pulse as shown in FIG. 3 alters temporally and spatially as shown in FIG. 4(a), (b) and (c). Therefore, the plasma emission intensity differs depending on the existing location of the particle, even though it has the same size. For instance, the case of the central position 0 and the edge position L of the sensitive region is shown in FIG. 5(a). FIG. 5(b) illustrates laser breakdown at positions O and L for a given particle size. FIG. 5(c) illustrates laser breakdown at location O for different particle sizes.

Figure 6:
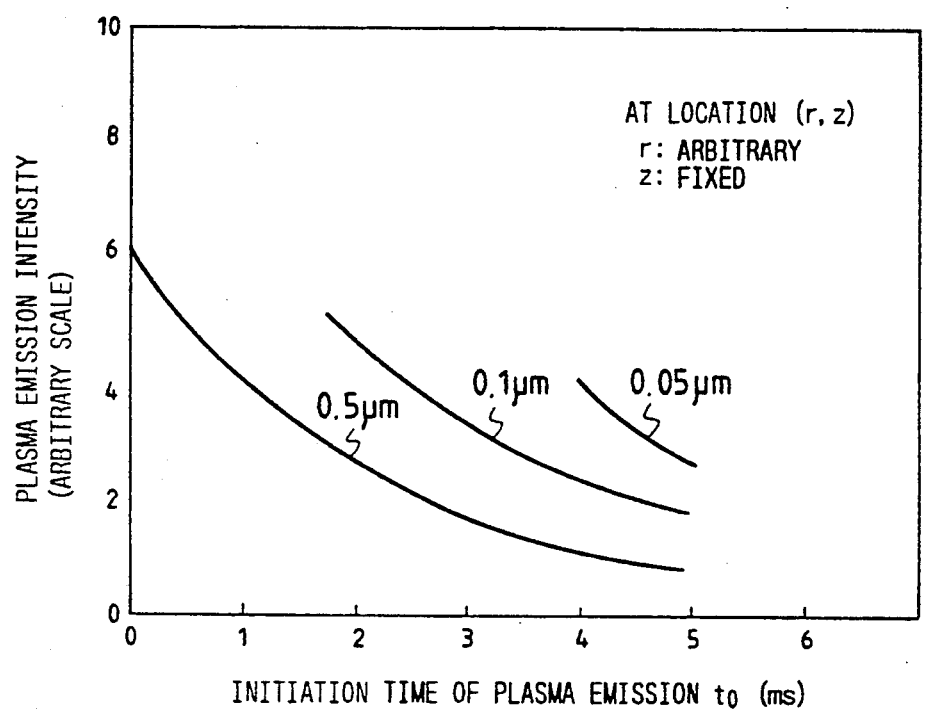
FIG. 6 is a graph showing the relation between the initiating time of plasma emission and the intensity of plasma emission.

In the present embodiment, each of photodetectors is arranged in axial direction with an interval of tens of μm, and the plasma emission is detected with the array photodetector 5 and the laser pulse 15 is detected with the photodetector 4. The-time difference detector 6 takes in both of outputs from the array photodetector 5 and the photodetector 4, detects the initiation time of the irradiation of the laser pulse with the output from the photodetector 4, and obtains the time from the initiation time of the irradiation of the laser pulse to the initiation time of the plasma emission which is detected from the output of the array photodetector 5, that is the item for the initiation of the plasma emission $t_0$. The observed data processor 9 detects the location of the particle in axial direction by finding which element in the array photodetector 5 detects the plasma emission. When plural elements detect the plasma emission, a processing in which the element of the maximum output is taken as the location of the particle is performed. And, the observed data processor 9 finds the intensity of the plasma emission by detecting the peak value of the intensity of the plasma emission at the particle location. In the data processor 13, the reference data such as FIG. 6 which shows the relation between the particle size and the location of the plasma emission in axial direction z, the intensity of the plasma emission $I_p$, or the initiation time of the plasma emission, which is determined previously with simulated particles, is provided. The reference data in FIG. 6 was obtained by adding polystyrene particles to ultrapure water as simulated particles. The data processor 13 obtains the particle size d from the reference data and such data as the initiation time of the plasma emission $t_0$ from the time difference detector 9, and the intensity of the plasma emission and the location of the plasma from the observed data processor 9. Then, the particle size distribution can be obtained by counting the number of the particles because the particle size can be measured as described above.

In the embodiment described above, the section of discrimination and counting of the particle 23 is able to obtain the particle size by simultaneous measurement of the initiation time and the intensity of the plasma emission with detecting only the coordinates z in axial direction of the laser pulse by the array photodetector for the location of the plasma emission ($r_0$, $z_0$), although the coordinates in radial direction r is not discriminated. In the present case, the particle size of 0.1 μm at least can be discriminated with reference to FIG. 6.

In the embodiment described above, intensity of sonic wave, can be used instead of the intensity of the plasma emission alternatively. And, as for information on the plasma emission waveform, the rise time of the emission, the fall time of the emission, or the duration time of the emission can be used instead of the initiation time of the emission alternatively. In that case, a waveform analyzer is used instead of the time difference detector in FIG. 1. The intensity of the incident laser pulse which is measured as the time base at the measurement of the initiation time of the emission can be used as a monitor for the intensity of the laser pulse. As for the time base, trigger pulse for operation of the pulse laser can be used. Further, the precision of the measurement can be improved more by providing a photodetector separately with the array photodetector and using both of the photodetectors as an apparatus having preferable resolving power of position and an apparatus having preferable resolving power of time respectively.

As described above, in the present embodiment, the measurement and counting of the particle size is possible without influence of the existing location of the particle by simultaneous measurement of the intensity of the plasma emission, the information on the plasma emission waveform, and the location of the plasma in the axial direction of the laser pulse.

And, it is possible to provide an apparatus for producing ultrapure water comprising an ultrapure water producing section, which is able to control the size of ultrafine particles in the ultrapure water till 0.1 μm at least, and a section for measurement and counting of the particle.

Further, it is possible to provide an apparatus for manufacturing of semiconductor having preferable yield and high reliability by cleaning wafers with the ultrapure water which is thoroughly controlled for the particles in the ultrapure water.

In the present embodiment, an apparatus for manufacturing of semiconductor using the ultrapure water is explained as an example, but it is naturally possible to utilize the present invention for producing and supplying apparatus of other liquids or gases, or other manufacturing apparatus for semiconductor etc. using the liquids and the gases described above.

Embodiment 2

Figure 7:
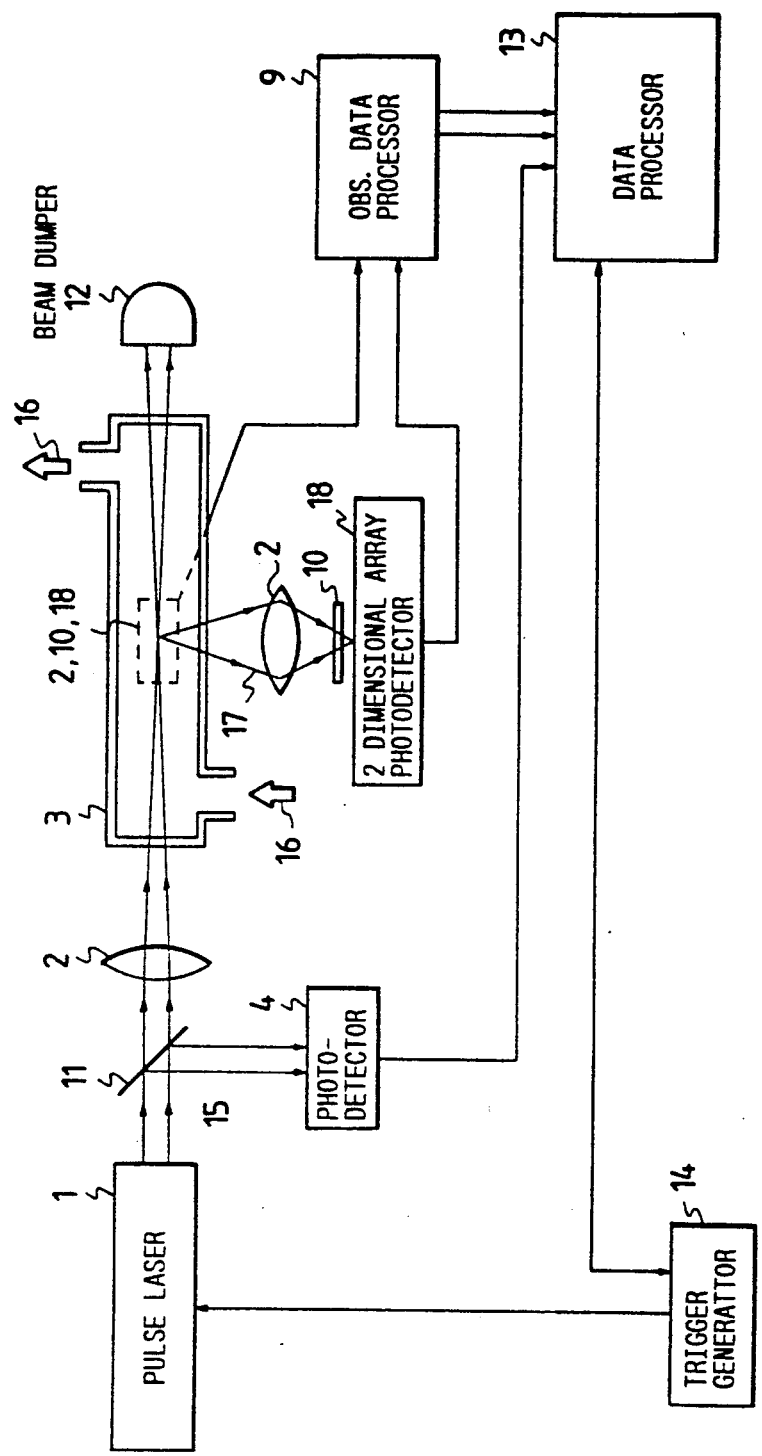
FIG. 7 is a schematic representation of the composition of the apparatus for measurement and counting of the particle in the second embodiment of the present invention.

The second embodiment of the section of the measurement and counting of the particle by the present invention is explained with referring to FIG. 7.

The present embodiment is an example that the particle size is measured and the number of the particles is counted by measuring of the location of the plasma generation (r, z) and intensity of the plasma emission. Accordingly, two two-dimensional array photodetectors 18 are used. In FIG. 7, same composing members as those shown in FIG. 1 have same numerals as those in FIG. 1. The two two-dimensional array photodetectors 18 are so arranged as to form as angle of 90° to the axis of the laser beam. The observed data processor 9 determines the coordinates of the plasma emission in the axial and radial direction of the laser beam as same as the first embodiment from the result of the two dimensional measurement on the location of the plasma emission in case of the observation from two different directions by 90°. Also, the observed data processor 9 detects the intensity of the plasma emission, as same as the first embodiment, by using either one of the two two-dimensional array photodetectors 18. Previously, the relation between the location of the plasma emission, the intensity of the plasma emission, and the particle size has been determined by experiments and been stored in the data processor 13 as a reference data. Then, the particle size d can be measured by comparison of the information from the observed data processor 9 with the reference data. As same as the previous embodiment, the diameter of the plasma or the intensity of the sonic wave, which is obtained by addition of a detecting system of sonic wave, can be used instead of the intensity of the plasma emission.

As described above, the measurement and counting of the particle size is possible by the simultaneous measurement of the information on the coordinates of the laser breakdown plasma and the intensity of the plasma emission in the present embodiment and, moreover, as the determination of the location of the plasma is possible, the present embodiment has an advantage to be able to discriminate the particle size for each laser breakdown even in a case the plural particles cause laser breakdown by one laser pulse.

Embodiment 3

Figure 8:
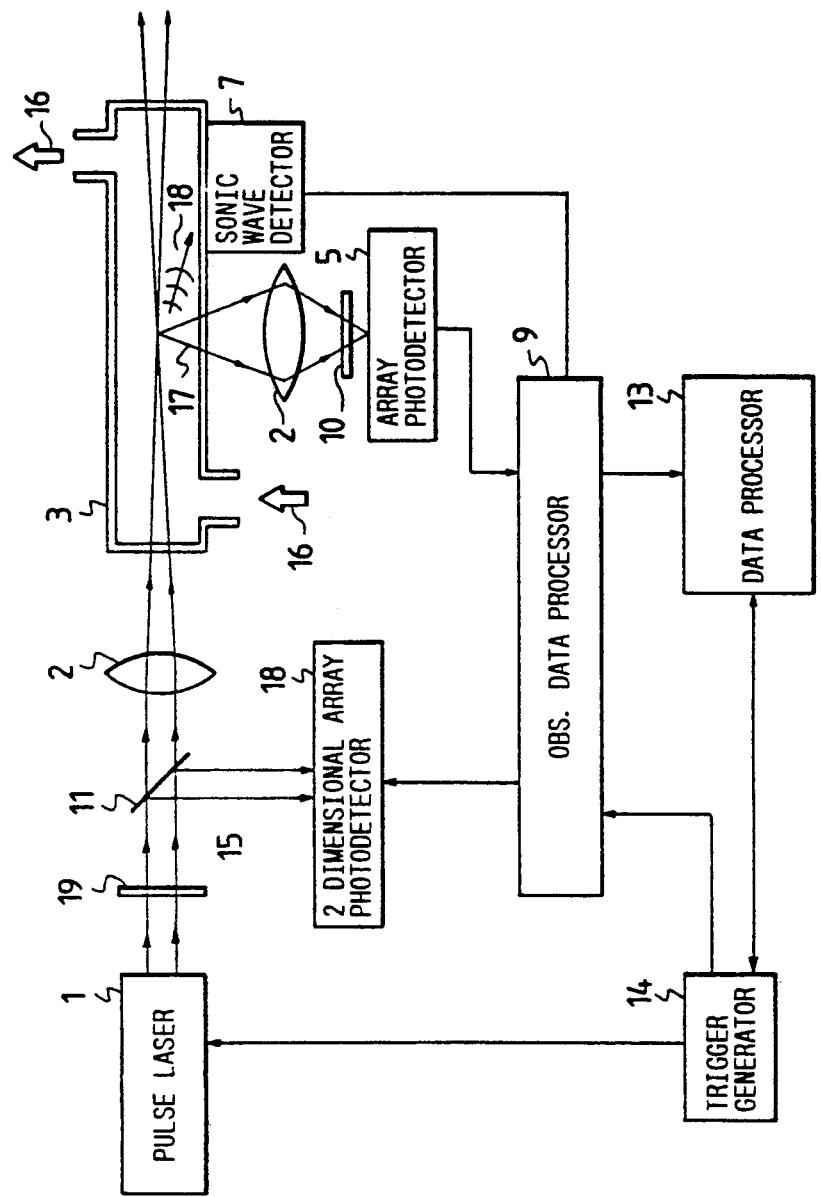
FIG. 8 is a schematic representation of the composition of the apparatus for measurement and counting of the particle in the third embodiment of the present invention.

The third embodiment of the measurement and counting of particles by the present invention is explained with referring to FIG. 8. In the present embodiment, the dependence of the particle size to the radial direction of the laser pulse 15 is reduced by flattening of the spatial distribution in the radial direction of the laser pulse intensity.

In the present embodiment, the spatial distribution in radial direction of the laser pulse intensity is controlled in super Gaussian mode by the soft filter 19. As the super Gaussian distribution is more uniform than ordinary Gaussian distribution and, moreover, the distribution after focusing by a lens has also same uniformity as before the focusing, the influence of intensity distribution of the laser pulse in radial direction can be reduced The plasma emission 17 which is generated in the focused region, where the laser pulse intensity is uniformed in radial direction by the method described above, is detected by photodetector 5, and the sonic wave of the breakdown is detected by the sonic wave detector 7. And, the observed data processor 9 determines the location of the plasma from the output of the photodetector 5 and the intensity of the sonic wave from the output of the sonic wave detector. Subsequently, as same as the first and second embodiments, the relation between the location of the plasma in axial direction of the laser pulse, the intensity of the sonic wave, and the particle size has been determined previously, and the particle size d is determined by detecting of the plasma location and the sonic wave intensity. The intensity distribution of the laser pulse in super Gaussian mode is monitored by the two-dimensional photodetector 18 whether the laser pulse has the predetermined distribution or not. Using the monitoring result, the distribution is calibrated by installing the soft filter 19, if necessary, or influence of the distribution fluctuation is calibrated by using the equation (1) etc. The monitoring of the intensity distribution in radial direction of the laser pulse is effective in improvement of measuring precision even in the previous two embodiments because the influence of the distribution fluctuation of the laser pulse intensity can be calibrated with the equation (1) etc. If the change with passage of the time is monitored, the precision can be improved further As explained above, in the present embodiment, the detection of a particle and measurement its size is possible from such two kinds of information as the location of the plasma in axial direction of the laser pulse and the intensity of the sonic wave by utilizing the laser pulse which is uniformed in radial direction. The uniformed spatial distribution of the intensity of the laser pulse is achieved by synthesis of laser pulses which have shifted optical axises each other. Similarly, the measurement of the particle size is possible from the intensity and the initiation time of the plasma emission or equivalent two kinds of information.

Embodiment 4

Figure 9:
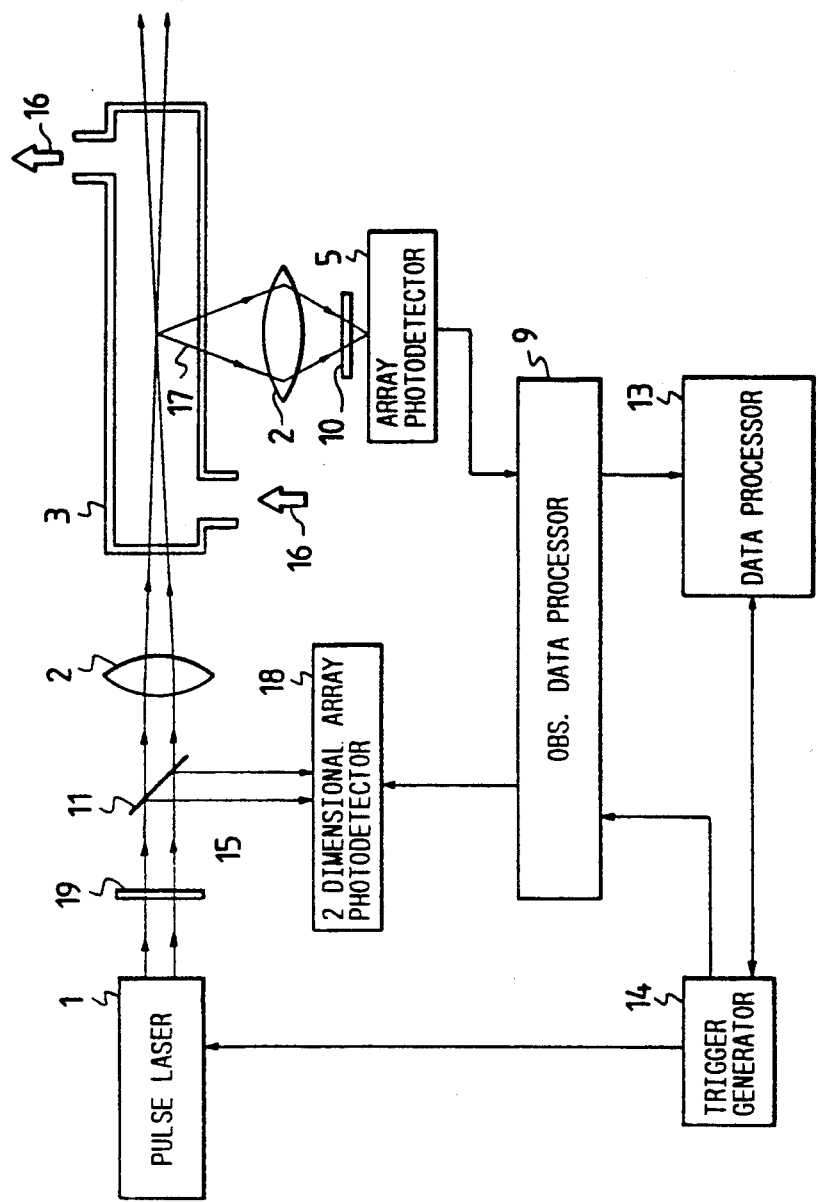
FIG. 9 is a schematic representation of the composition of the apparatus for measurement and counting of the particle in the further embodiment of the present invention.
Figure 10A:
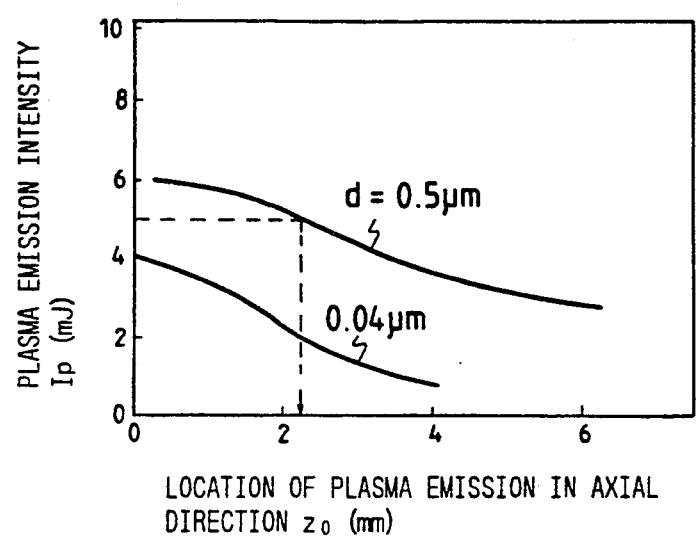
FIG. 10(a)–(b) are graphs for explanation of the relation between the intensity of plasma emission, the initiation time of the plasma emission, and the particle size based on the position of the plasma emission in axial direction.
Figure 10B:
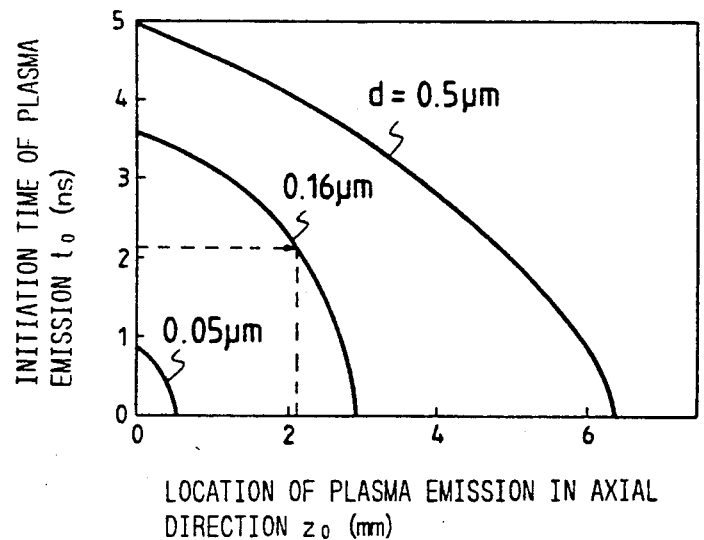

Next, the fourth embodiment of the section of the measurement and counting of the particle by the present invention is explained with referring to FIG. 9 and 10. The present embodiment is a method for measurement of the particle size in preferable precision without detecting the location of the laser breakdown plasma. In the present embodiment, the dependence of the intensity of the laser pulse 15 on radial direction is reduced by the soft filter 19 as same as the third embodiment, and the intensity distribution in radial direction is monitored by the two-dimensional array photodetector 18. The waveform of the plasma emission is detected by the photodetector 5, and the intensity of the plasma emission $I_p$ is determined by the observed data processor 9 as same as the third embodiment. Further, the observed data processor 9 determines the initiation time of the pulse laser oscillation with the trigger signal from the trigger generator 14, and the photodetector 5 detects the initiation time of the plasma emission, subsequently, the initiation time $t_0$ of the plasma emission is obtained from the difference of the two kinds of information. FIG. 10 illustrates the experimental result on the intensity of the plasma emission $I_p$ (FIG. a) and the initiation time of the plasma emission $t_0$ (FIG. b) versus the position of the plasma in axial direction $z_0$. The above experimental data are stored in the data processor 13 as the reference data. For instance, when intensity of the plasma emission $I_p = 5$ mJ, and the initiation time of the plasma emission $t_0 = 2.2$ ns are determined by the observed data processor 9, referring to FIG. 10 (a) determines that the location of the plasma in axial direction $z_0$ is nearly 2.25 mm at $I_p = 5$ mJ, and from the obtained location $z_0$ and the initiation time of the plasma emission $t_0$, and referring to FIG. 10 (b), the particle size of about 0.16 μm can be obtained. Naturally, as the reference data which is stored in the data processor 13 is discrete, the values in intervals are interpolated. The data in FIG. 10 is based on the position of the plasma in axial direction, but the data can be used as a reference data by modifying directly to the relation between the intensity of the plasma emission $I_p$ and the initiation time of the plasma emission $t_0$. According to the experimental data shown in FIG. 10, the particle size of at least 0.1 μm can be measured.

The embodiment described above is an example in which the dependence of the plasma emission intensity on the particle position in radial direction is reduced, but as explained in the second embodiment, even in the case without calibration of the dependence on the radial direction, the particle size can be measured precisely although the precision in the particle size measurement is somewhat inferior to the case with the calibration.

As explained above, by the present embodiment, particles in liquid can be measured precisely without detecting the location of the laser breakdown plasma.

Embodiment 5

Figure 11:
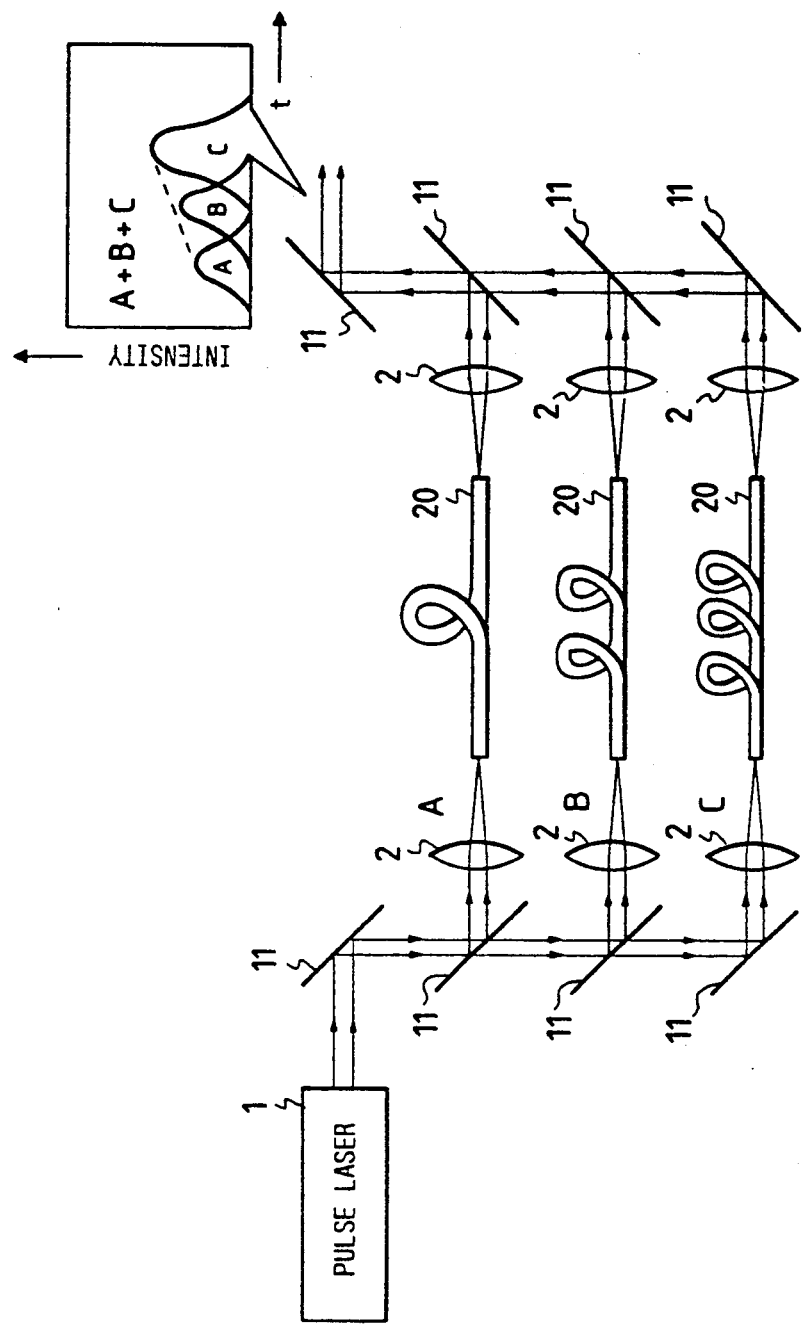
FIG. 11 is a schematic representation of the composition of a portion of the apparatus for measurement and counting of the particle in the fifth embodiment of the present invention.

Next, the fifth embodiment of the section of measurement and counting of the particle is explained with referring to FIG. 11. The composition shown in FIG. 11 is installed before the beam splitter 11 in FIG. 1. In the present embodiment, plural laser pulses are generated with combinations of plural optical fibers 20 having different length and plural beam splitters 11 having different reflectance. Then, the laser pulse having moderate rise time is synthesized with the pulses having different intensity and delay time at the final beam splitter, and is lead to the sample cell. Using the laser pulse, when the information on the waveform such as the initiation time of the plasma emission are measured by the similar composition of the apparatus as FIG. 1, the difference of the initiation time of the plasma emission which depends on the difference of the particle size is enlarged on time axis because of the expanded rise time of the laser pulse, consequently, the measurement precision of the initiation time of the plasma emission is improved. Similarly, the measurement of the intensity of the plasma emission which depends on the integrated intensity of the laser pulse after the initiation time is improved. Accordingly, as the resolution of time is relatively improved by using the laser pulse having moderate rise time, the precision of the measurement of the particle size is improved. The waveform of the laser pulse can be changed by controlling of the pulse laser itself.

Embodiment 6

Figure 13A:
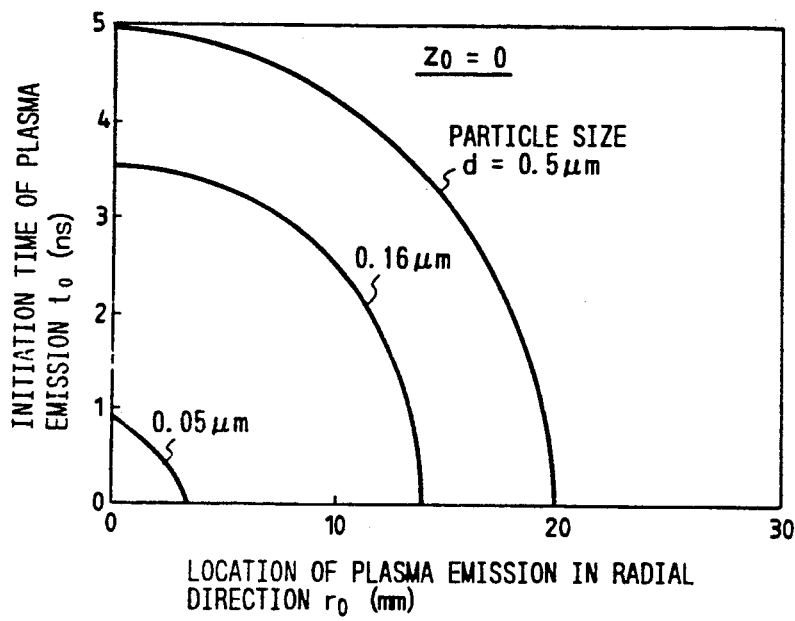
FIG. 13 (a) is a graph showing the relation between the radial position of plasma emission and the initiation time of the plasma emission at the axial direction of the plasma emission $Z_0 = 0$.
Figure 13B:
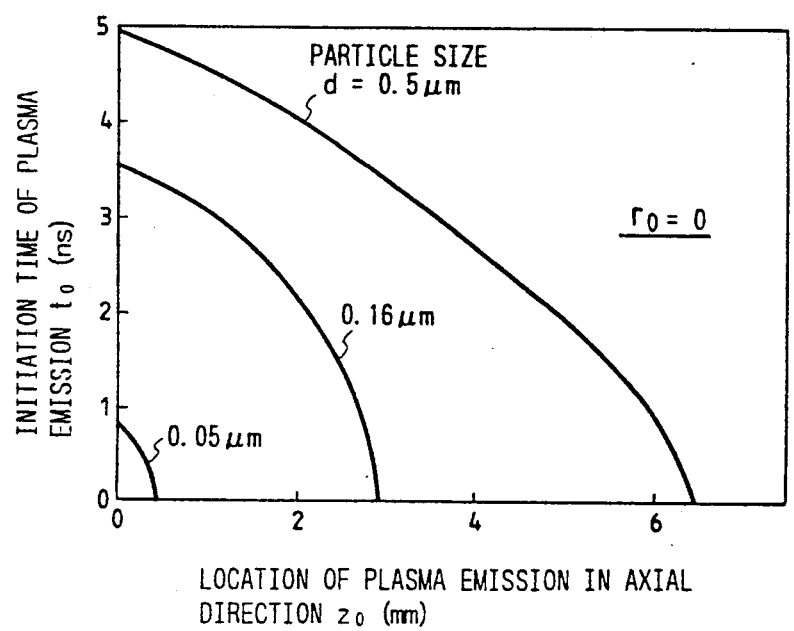
Figure 14A:
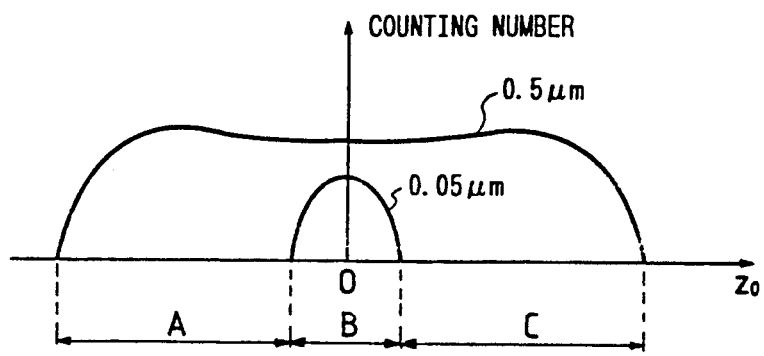
FIG. 14(a)-(b) are schematic drawing showing the relation of the diameter of the plasma emission and the particle size.
Figure 14B:
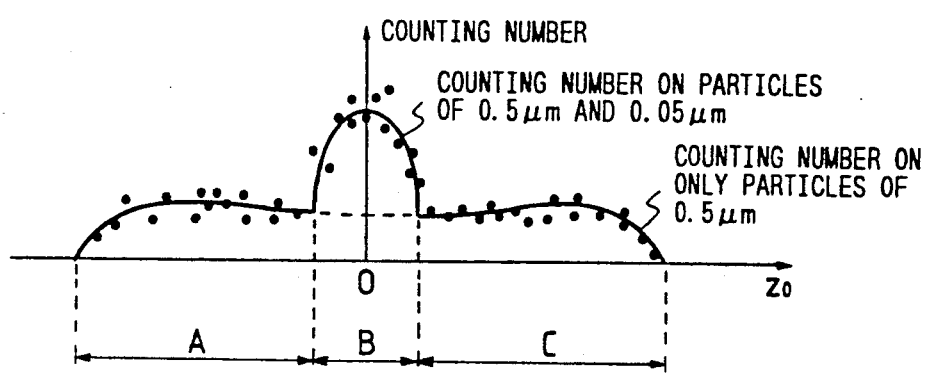

The sixth embodiment of the section of measurement and counting of the particle of the present invention is explained with referring to FIGS. 12 to 14. FIG. 12 illustrates the composition of the section of measurement and counting of the particle. FIG. 13 shows the spatial distribution of the initiation time of the plasma emission at the location of axial direction $z_0 = 0$ and of radial direction $r_0 = 0$. The initiation time in FIG. 13 is different from the previous initiation time, which is defined as the time from the initiation of the laser pulse irradiation to the initiation of the plasma emission, and indicates the time from the initiation of the plasma emission to the time when the laser pulse reaches its peak. Therefore, the larger the particle size is, the longer the initiation time of the plasma emission becomes. FIG. 14 shows the experimental result of obtaining of the particle size from the spatial distribution of the plasma. In the previous embodiments, the particle size is determined individually from at least two kinds of observed values. However, if individual measurement of the particle size is give up, the particle size distribution can be obtained from only one kinds of information.

In the present embodiment, only the coordinates $z_0$ of the location of the plasma in axial direction of the laser pulse are measured by the array photodetector 5. After continuating of the measurement until a counted number during a predetermined time or of a predetermined number is obtained, the particle size is measured from the dependence of the counted number on $Z_0$, and the concentration of each particle size is calculated by the data processor 13.

The volume of the sensitive region of the laser breakdown depends on the particle size as shown in FIG. 3, and the larger the particle size is, the wider the sensitive region expands along optical axial direction. Accordingly, for instance, in the case of discriminating two particle size of 0.5 μm and 0.05 μm, as only 0.5 μm particle is measured at the region A and both of 0.5 μm and 0.05 μm particles are measured in the region B in FIG. 14, the concentration of 0.05 μm particle is calculated first by fitting of the volume of the sensitive portion of 0.5 μm to the counted number distribution, subsequently, after the contribution of 0.5 μm particle to the counted number in the region B is subtracted using the calculated concentration described above, the concentration of 0.05 μm particle can be obtained by fitting of the volume of the sensitive region of 0.05 μm particle to the counted number distribution as same as before. The resolution of the particle size can be improved by dividing the steps described above finer. As described above, by the present embodiment, the particle size of at least 0.1 μm can be measured using only the spatial distribution of the plasma.

In each of the embodiments described above, in view of the improvement of the precision of the measurement, enlarging of the sensitive region is preferable in aspect of the precision of the measurement on the location of the plasma emission.

Further, in the measurement of particle size distribution and number density of the particulate material in the ultrapure water, the reliability of the measurement can be improved by using such conventional methods having satisfactory effects to relatively large particle size as represented by the light scattering method together with the laser breakdown method, and with using the measured result on the relatively large particle size by the conventional method is evaluated with equal or rather more weight to the measured result by the laser breakdown method and, while, the measured result by the laser breakdown method is evaluated on the relatively small particle size.

The system described above is applicable to the apparatus for producing other liquids or gases of high purity in addition to ultrapure water, and to the manufacturing processes using same.

What is claimed is:

1. An apparatus for analyzing a particulate material by irradiation of a laser pulse having sufficient energy to cause laser breakdown of the particulate material existing in liquid, comprising:
    first means for detecting an intensity of a plasma emission emitted by the laser breakdown of the particulate material in the liquid,
    a second means for detecting a location where the laser breakdown occurs,
    third means for detecting a waveform of the plasma emission by the laser breakdown, and
    means for measuring a particle size of the particulate material in accordance with outputs from at least two of said first, second and third means for detecting.

2. An apparatus for analyzing a particulate material by irradiation of a laser pulse having sufficient energy to cause laser breakdown of the particulate material existing in liquid, comprising:
    first means for detecting an intensity of a plasma emission emitted by the laser breakdown of the particulate material in the liquid,
    a second means for detecting a location where the laser breakdown occurs,
    third means for detecting a waveform of the plasma emission by the laser breakdown, and
    means for measurement of a particle size of the particulate material in accordance with outputs from at least two of said first, second and third means for detecting.

3. An apparatus for analyzing a particulate material by irradiation of a laser pulse having sufficient energy to cause laser breakdown of the particulate material existing in liquid, comprising:
    means for detecting an intensity of a plasma emission emitted by the laser breakdown of the particulate material in the liquid and information other than the intensity of the plasma emission, and
    means for measurement of a particle size of the particulate material in accordance with said intensity of the plasma emission and said information of the plasma emission other than the intensity of the plasma.

4. An apparatus for analyzing a particulate material by irradiation of a laser pulse having sufficient energy to cause laser breakdown plasma emission of the particulate material existing in liquid, comprising:
    means for measuring a particle size of the particulate material in accordance with an intensity of the laser breakdown plasma emission of the particulate material in the liquid, and for calibrating said particle size with information other than the intensity of the laser breakdown plasma emission.

5. An apparatus for analyzing a particulate material by irradiation of a laser pulse having sufficient energy to cause laser breakdown of the particulate material existing in liquid, comprising:
    first means for detecting an intensity of a plasma emission emitted by the laser breakdown of the particulate material in the liquid,
    a second means for detecting a location where the laser breakdown occurs, and
    means for measuring a particle size of the particulate material in accordance with outputs from said first means for detecting an intensity and said second means for detecting a location.

6. An apparatus for analyzing a particulate material by irradiation of a laser pulse having sufficient energy to cause laser breakdown of the particulate material existing in liquid, comprising:
    first means for detecting a location where the laser breakdown of the particulate material in the liquid occurs,
    second means for detecting a waveform of a plasma emission emitted by the laser breakdown, and
    means for measurement of a particle size of the particulate material in accordance with outputs from said first means for detecting and said second means for detecting.

7. An apparatus for analyzing a particulate material by irradiation of a laser pulse having sufficient energy to cause laser breakdown of the particulate material existing in liquid, comprising:
    means for detecting a waveform of plasma emission which is generated at said laser breakdown of the particulate material in the liquid,
    means for detecting a location of said plasma emission, and
    means for measurement of a particle size of the particulate material in accordance with outputs from said means for detecting a waveform and said means for detecting a location.

8. An apparatus for analyzing a particulate material by irradiation of a laser pulse having sufficient energy to cause laser breakdown of the particulate material existing in liquid, comprising:
    means for detecting a sonic wave which is generated at said laser breakdown of the particulate material in the liquid,
    means for detecting an initiation time of a plasma emission emitted by the laser breakdown, and
    means for measurement of a particle size of the particulate material in accordance with a previously determined relation between information obtained from said sonic wave, said initiation time of the plasma emission, and the particle size of the particulate material, and outputs from said means for detecting a sonic wave and said means for detecting an initiation time.

9. An apparatus for analyzing a particulate material by irradiation of a laser pulse having sufficient energy to cause laser breakdown of the particulate material existing in liquid, comprising:

means for detecting a plasma emission which is generated at said laser breakdown of the particulate material in the liquid, means for detecting a location where said laser breakdown occurs, and means for measurement of a particle size of the particulate material in accordance with a previously determined relation between information obtained from an intensity of said plasma emission, said location of said laser breakdown plasma, and the particle size of the particulate material, and outputs from said means for detecting a plasma emission and said means for detecting a location.

10. An apparatus for analyzing a particulate material by irradiation of a laser pulse having sufficient energy to cause laser breakdown of the particulate material existing in liquid, comprising:

means for detecting a location of a plasma emission which is generated at said laser breakdown of the particulate material in the liquid, means for measurement of a particle size of the particulate material in accordance with a previously determined relation between respective outputs of said two means for detecting and said particle size of the particulate material.

11. An apparatus for analyzing a particulate material by irradiation of a laser pulse having sufficient energy to cause laser breakdown of the particulate material existing in liquid, comprising:

means for detecting a sonic wave which is generated at said laser breakdown of the particulate material in the liquid, means for detecting a plasma emission which is generated by said laser breakdown, means for detecting an initiation time of said plasma emission, and means for measurement of a particle size in accordance with a previously determined relation between respective three kinds of information obtained by said three means for detecting and said particle size of the particulate material.

12. An apparatus for analyzing a particulate material by irradiation of a laser pulse having sufficient energy to cause laser breakdown of the particulate material existing in liquid, comprising:

means for detecting an intensity of a plasma emission which is generated by said laser breakdown of the particulate material in the liquid, and means for measurement of a particle size of the particulate material in accordance with output from said means for detecting.

13. An apparatus for analyzing a particulate material by irradiation of a laser pulse having sufficient energy to cause laser breakdown of the particulate material existing in liquid, comprising:

means for generating said laser pulse, and means for measuring a particle size of the particulate material in the liquid by flattening an intensity of said laser pulse in vertical direction to an irradiating direction of said laser pulse.

14. An apparatus for analyzing a particulate material by irradiation of a laser pulse having sufficient energy to cause laser breakdown of the particulate material existing in liquid, comprising:

means for generating said laser pulse, and means for measuring a particle size of the particulate material in the liquid by calibrating an error depending on an intensity distribution of said laser pulse in a radial direction of said laser pulse.

15. An apparatus for analyzing a particulate material by irradiation of a laser pulse having sufficient energy to cause laser breakdown of the particulate material existing in liquid, comprising:

means for generating said laser pulse, and means for measuring a particle size of the particulate material in the liquid by irradiating with said laser pulses, wherein each laser pulse occurs in accordance with a respective time delay.

16. An apparatus for analyzing a particulate material by irradiation of a laser pulse having sufficient energy to cause laser breakdown of the particulate material existing in liquid, comprising:

means for generating said laser pulse, and means for measuring a particle size of least 0.1 $\mu$m by means for calibrating said particle size in accordance with an intensity of a plasma emission or a sonic wave generated by said laser breakdown of the particulate material in the liquid.

17. An apparatus for analysis of a particulate material, comprising:

first apparatus for analysis of said particulate material by irradiation of a laser pulse having sufficient energy to cause laser breakdown of the particulate material existing in liquid, second apparatus for analysis of particulate material by any of a light scattering method, a light transmission method, and an electroresistance method, and means for controlling an analysis of said particulate material, wherein in case of a particle size of said particulate material is larger than a set value, the first and the second apparatus for analysis of said particulate material are used, and, in case of the particle size of said particulate material is smaller than the set value, the first apparatus of analysis of said particulate material is used.

18. An apparatus for analysis of a particulate material, comprising:

first apparatus for analysis of said particulate material by irradiation of a laser pulse having sufficient energy to cause laser breakdown of the particulate material existing in liquid, second apparatus for analysis of particulate material which analyzes the particulate material without causing said laser breakdown, and means for controlling an analysis of said particulate material in the liquid, wherein in case of a particle size of said particulate material is larger than a value, the first and the second apparatus for analysis of said particulate material are used, and, in case of the particle size of said particulate material is smaller than the a set value, the first apparatus for analysis of said particulate material is used.

19. An analytical method for determined a particle size of particulate material by irradiation of a laser pulse having sufficient energy to cause breakdown of the particulate material existing in liquid, comprising the steps of
  (a) selecting at least two of the following:
    (i) detecting an intensity of a plasma emission emitted by the laser breakdown of the particulate material in the liquid or a sonic wave generated by the laser breakdown,
    (ii) detecting a location of the plasma emission, and
    (iii) detecting a plasma emission waveform; and
  (b) measuring said particle size of the particulate material in accordance with information obtained from step (a).

20. An analytical method for determined a particle size of particulate material by irradiation of a laser pulse having sufficient energy to cause breakdown of the particulate material existing in liquid, comprising the steps of:
  obtaining said particle size of the particulate material from an intensity of a plasma emission emitted by the laser breakdown of the particulate material in the liquid or a sonic wave generated by the laser breakdown, and
  calibrating said particle size with information other than the intensity of the plasma emission or the sonic wave.

21. An analytical method for determined a particle size of particulate material by irradiation of a laser pulse having sufficient energy to cause breakdown of the particulate material existing in liquid, comprising the steps of:
  (a) selecting at least two of the following:
    (i) detecting an intensity of a plasma emission emitted by the laser breakdown of the particulate material in the liquid or a sonic wave generated by the laser breakdown,
    (ii) detecting a location of the plasma emission, and
    (iii) detecting a plasma emission waveform; and
  (b) measuring particle size of the particulate material in accordance with a relation between information which is obtained from step (a) and said particle size of the particulate material.

22. An apparatus for producing ultra pure water, comprising:
  a section for producing ultrapure water,
  means for irradiation of a laser pulse having sufficient energy to cause laser breakdown of a particulate material existing in the ultra pure water produce by said apparatus for producing ultrapure water,
  first means for detecting an intensity of a plasma emission emitted by the laser breakdown of the particulate material in the ultrapure water or a sonic wave generated by the laser breakdown,
  second means for detecting a location of where the laser breakdown occurs,
  third means for detecting a plasma emission waveform,
  an analytical section for measuring a particle size and detecting a concentration of the particulate material based on outputs from at least two of said first, second and third means for detecting, and
  a control section for controlling the section for producing ultrapure water based on the particle size and the concentration which are determined at said analytical section.

23. An apparatus for producing ultra pure water, comprising:
  a section for producing ultrapure water,
  means for irradiation of a laser pulse having sufficient energy to cause laser breakdown of a particulate material existing in the ultrapure water,
  an analytical section for measuring a particle size and detecting a concentration of the particulate material based on an intensity of a plasma emission emitted by the laser breakdown of the particulate material in the ultrapure water or a sonic wave generated by the laser breakdown and information other than the intensity of said plasma emission or said sonic wave, and
  a control section for controlling the section for producing ultrapure water based on the particle size and the concentration which are determined at said analytical section.

24. An apparatus for producing ultrapure water, comprising:
  a section for producing ultrapure water,
  means for irradiation of a laser pulse having sufficient energy to cause laser breakdown of a particulate material existing in the ultrapure water,
  an analytical section for measuring a particle size and detecting a concentration of the particulate material based on an intensity of a plasma emission emitted by the laser breakdown of the particulate material in the ultrapure water or a sonic wave generated by the laser breakdown and information other than the intensity of said plasma emission or said sonic wave, and
  a control section for controlling the section for producing ultrapure water based on the particle size and the concentration which are determined at said analytical section.

25. An apparatus for producing ultrapure water, comprising:
  a section for producing ultrapure water,
  means for irradiation of a laser pulse having sufficient energy to cause laser breakdown of a particulate material existing in the ultrapure water,
  an analytical section for measuring a particle size of at least 0.1 $\mu$m by calibrating the particle size of the particulate material which is measured by an intensity of a plasma emission emitted by the laser breakdown of the particulate material in the ultrapure water or a sonic wave by said laser breakdown, and detecting a concentration of the particulate material, and
  a control section for controlling the section for producing ultrapure water based on the particle size and the concentration which are determined at said analytical section.

26. An apparatus for producing pure gas, comprising:
  a section for producing pure gas,
  means for irradiation of irradiating a particulate material existing in the gas which is produced at said section for producing pure gas with a laser pulse having sufficient energy to cause laser breakdown,
  an analytical section, for analysis of the particulate material, by discrimination of a particle size and detection of a concentration of the particulate material in accordance with an intensity of a plasma emission emitted by the laser breakdown of the particulate material in the gas or a sonic wave by the laser breakdown and information other than the intensity of the plasma emission or the sonic wave, and
  a control section for controlling the section for producing pure gas based on the particle size and concentration which are measured at said analytical section.

27. An apparatus according to claim 1, wherein the liquid is ultrapure water and the means or measurement of particle size includes means for detecting concentration of the particulate material based on the output from at least said two means for detecting, and further comprising a control section for controlling means for producing ultrapure water in accordance with the measured particle size and detected concentration.

28. An apparatus according to claim 27, further comprising means for transmitting the produced ultrapure water to a wafer washing section for washing a wafer during manufacture of a semiconductor wafer, and control means for controlling the manufacturing of a semiconductor in accordance with the measured particle size and detected concentration.

29. An apparatus according to claim 12, wherein said intensity of a plasma emission is optically detected.

* * * * *